United States Patent [19]
Smith et al.

[11] Patent Number: 5,962,520
[45] Date of Patent: Oct. 5, 1999

[54] HYDROLYTICALLY UNSTABLE, BIOCOMPATIBLE POLYMER

[75] Inventors: Daniel J. Smith, Stow; Weisun Rao, Akron, both of Ohio

[73] Assignee: The University of Akron, Akron, Ohio

[21] Appl. No.: 09/054,098

[22] Filed: Apr. 2, 1998

[51] Int. Cl.⁶ .................................................. A61K 31/215
[52] U.S. Cl. ........................ 514/529; 514/533; 514/772.3; 514/772.4; 514/772.6; 514/784; 514/785; 526/311; 528/291; 528/292; 424/439; 424/486; 424/487; 424/497; 560/157; 560/169
[58] Field of Search ..................... 514/529, 533, 514/772.3, 772.4, 772.6, 784, 785; 526/311; 528/291, 292; 424/439, 486, 487, 497; 560/157, 169

[56] References Cited

U.S. PATENT DOCUMENTS

| | | | |
|---|---|---|---|
| 5,039,705 | 8/1991 | Keefer et al. | 514/611 |
| 5,155,137 | 10/1992 | Keefer et al. | 514/611 |
| 5,405,919 | 4/1995 | Keefer et al. | 525/377 |
| 5,632,981 | 5/1997 | Saavedra et al. | 424/78.08 |
| 5,650,447 | 7/1997 | Keefer et al. | 514/772.4 |
| 5,691,423 | 11/1997 | Smith et al. | 525/377 |

OTHER PUBLICATIONS

Polycondensation of ω–aminoalkylamino acid esters, Asahara, T.; Die Makro. Chemie, 136(3391), 211–219, 1970.

New nitric oxide–releasing zwitterions derived from polyamines, Hrabie et al., J. Org. Chem., 58(6), 1472–1476, 1993.

Nitric oxide–releasing polymers containing the [N(O)NO]⁻ group, Smith, et al., J. Med. Chem., 39:5, 1148–1155 1996.

*Primary Examiner*—Samuel Barts
*Attorney, Agent, or Firm*—Renner, Kenner, Greive, Bobak, Taylor & Weber

[57] ABSTRACT

A hydrolytically unstable, biocompatible polymer capable of carrying and releasing a pharmaceutical compound when introduced into physiological media. In a preferred embodiment, the polymer contains ester linkages that are susceptible to hydrolytic degradation. A monomeric unit of the polymer can also be used as a hydrolytically unstable linking agent for quickening the degradation of polymers, particularly cross-linked polymers.

11 Claims, 8 Drawing Sheets

HYDROLYTICALLY UNSTABLE, BIOCOMPATIBLE POLYMER

TECHNICAL FIELD

The present invention generally relates to biodegradable polymers useful as carriers of pharmaceutical compounds and as degradation agents. More specifically, the present invention relates to biodegradable, water-soluble polyester resins containing derivatizable secondary amine groups capable of carrying pharmaceutical compounds such as nitric oxide (NO). The present invention also relates to a method for the synthesis of such polyester amines.

BACKGROUND OF THE INVENTION

Biodegradable polymers are one of the most common types of carriers used in controlled drug delivery systems. A controlled drug delivery system is normally one where the rate of drug delivery is in a predesigned mode and is delivered over extended periods, such as days, weeks or even months.

Low molecular weight polymers have been used as carriers of pharmaceutical compounds; however, they must be chemically manipulated to prevent their absorption into the bloodstream because quick absorption can cause cytotoxicity. Also, low molecular weight polymers tend to degrade quickly, thus inhibiting their ability to provide controlled delivery over a significant period of time.

High molecular weight carriers are also known. These carriers, however, tend to take a long time to degrade and be cleared from the body. The slow clearance of high molecular weight polymers can have deleterious effects on the body, such as cumulative toxicity to the kidney or liver. Also, although a polymer, per se, may not have adverse effects on an organism, the byproducts of degradation of that polymer may be toxic or have other deleterious effects on the organism.

Thus, there is a need for a readily degradable, biocompatible, high molecular weight polymer capable of controlled delivery of a pharmaceutical compound within an organism.

SUMMARY OF THE INVENTION

It is therefore a primary object of the present invention to provide a hydrolytically unstable, biocompatible polymer.

It is another object of the present invention to provide a carrier that is capable of delivering and releasing a biologically active moiety or other agent to the specific area within the body where it is introduced without disseminating uncontrollably throughout the body.

It is yet another object of the present invention to provide a carrier that releases nitric oxide or other pharmaceutical compounds then quickly biodegrades into naturally occurring compounds at various pH levels following release.

It is still yet another object of the present invention to provide a compound that can be inserted into a polymer to facilitate the degradation of the polymer.

It is still a further object of the present invention to provide a method for controlling the rate of pharmaceutical release by the amount of NO loading.

It is another object of the present invention to provide a method of controlling the rate of polymer degradation by the amount of NO loading.

At least one of the foregoing objects of the present invention, together with the advantages thereof over existing pharmaceutical compounds, which shall become apparent from the specification that follows, are accomplished by the invention as hereinafter described and claimed.

In general, the present invention provides a hydrolytically unstable polymer comprising a carrier having the formula (I):

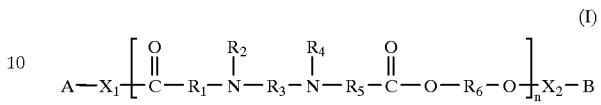

wherein A is a functional group; $X_1$ is the monomer fragment —$(R_3)NR_4(R_5)COO(R_6)O$—; B is a functional group; $X_2$ is the monomer fragment —$OC(R_1)NR_2(R_3)$—; $R_1$ and $R_5$ are each independently selected from organic groups containing from about 1 to about 10 carbon atoms; $R_2$ and $R_4$ are each independently selected from hydrogen or organic groups containing from 1 to about 20 carbon atoms or a pendant polymer chain having a molecular weight less than about 5000; $R_3$ is independently selected from organic groups containing from 1 to about 10 carbon atoms; $R_4$ is independently selected from organic groups containing from about 1 to about 10 carbon atoms; and n is a positive integer.

PREFERRED EMBODIMENT FOR CARRYING OUT THE INVENTION

Figure 1:
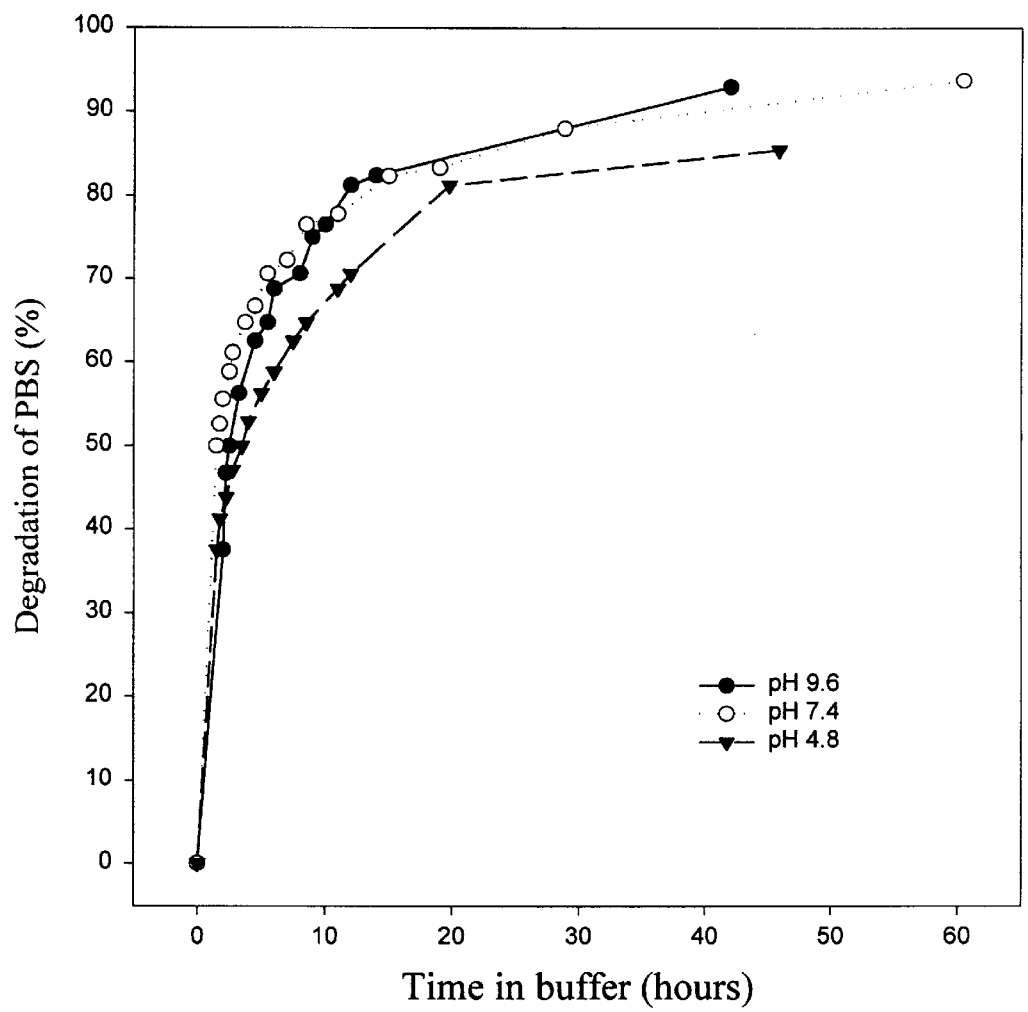
FIG. 1 compares degradation rates of poly(butanediol spermate) (PBS) in buffers of various pH at 20° C.
Figure 2:
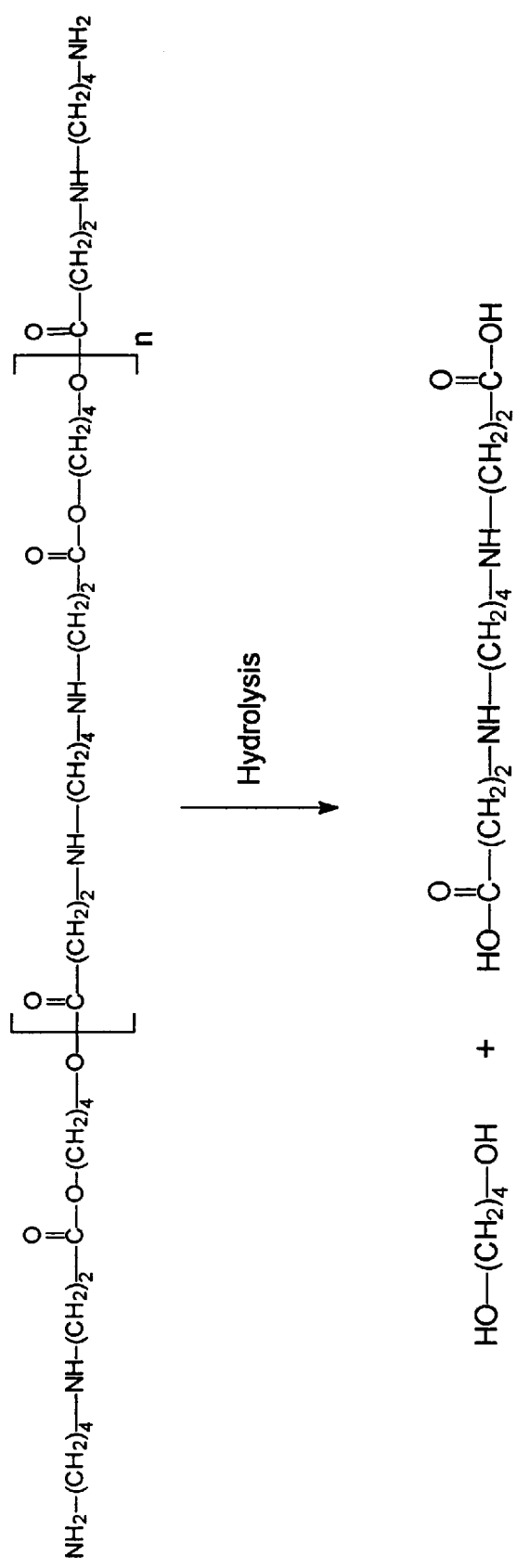
FIG. 2 represents the hydrolysis of poly(butanediol spermate) into 1, 4-butanediol and spermic acid.

The compounds of the present invention are hydrolytically unstable polyesters containing derivatizable groups. The derivatizable groups are functional groups, such as amines, that readily react with other compounds, such as pharmaceutical compounds, that become bound ("loaded") to the polymer. The compound of the present invention acts as a carrier in some preferred embodiments, controllably releasing loaded pharmaceutical compounds. It is a hydrolytically unstable polyester because, as shown in FIG. 1, it rapidly degrades in an aqueous buffer. FIG. 2, for example, shows the hydrolytic degradation reaction of poly (butanediol spermate) into 1,4-butanediol and spermic acid.

The compound of the present invention can generally be defined by the formula (I)

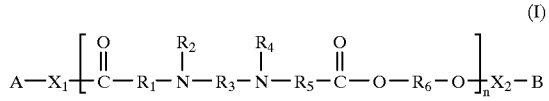

(I)

wherein A is a functional group; $X_1$ is the monomer fragment —$(R_3)NR_4(R_5)COO(R_6)O$—; B is a functional group; $X_2$ is the monomer fragment —$OC(R_1)NR_2(R_3)$—; $R_1$ and $R_5$ are each independently selected from organic groups containing from about 1 to about 10 carbon atoms; $R_2$ and $R_4$ are each independently selected from hydrogen or organic groups containing from 1 to about 20 carbon atoms or a pendant polymer chain having a molecular weight less than about 5000; $R_3$ is independently selected from organic groups containing from 1 to about 10 carbon atoms; $R_6$ is independently selected from organic groups containing from about 1 to about 10 carbon atoms; and n is a positive integer.

A and B are independently selected and are preferably a hydroxyl group or an amino group. $R_1$ and $R_5$ preferably have from about 2 to about 6 carbon atoms and more preferably from about 2 to about 4 carbon atoms. $R_2$ and $R_4$ preferably have at least some hydrophilic character and are preferably selected from hydrogen or organic groups containing from 1 to about 6 carbon atoms. More preferably, $R_2$ and $R_4$ are both hydrogen atoms. $R_3$ preferably has from about 2 to about 6 carbon atoms, and more preferably from about 3 to about 5 carbon atoms. $R_6$ is preferably biocompatible when it is isolated from the polymer, such as HO—$R_6$—OH. One of skill in the art would be able to determine, without undue experimentation, the size of $R_6$ that would render it biocompatible. Preferably, $R_6$ has from about 2 to about 6 carbon atoms, and more preferably from about 2 to about 4 carbon atoms.

The size of n, the number of monomer units, reflects the molecular weight of the polymer of the present invention. It is contemplated that n is preferably from about 5 to about 1000 and more preferably from about 5 to about 60. Accordingly, the molecular weight of the polymer of the present invention, excluding polymeric side chains, if any, can be from about 1000 to about 100,000. The skilled artisan will appreciate that the molecular weight should be in a range that provides a half-life within the body suitable to the application; the half-life is proportional to the molecular weight and is easily determined.

An "organic group" or "organic radical," as used herein, is intended to refer to those compounds of carbon generally considered to fall in the realm of "organic chemistry." This includes straight-chain aliphatics, cyclics (alicyclics and aromatic hydrocarbons and heterocyclics), combinations of aliphatic and cyclic structures, organometallic compounds, and polymers.

In a preferred embodiment of the present invention, $R_1$ and $R_5$ are each independently selected from an alkyl group, an aryl group, an alkyl halide, or an aryl halide; $R_2$ and $R_4$ are each independently selected from hydrogen, an alkyl group, an aryl group, or a pendant polymer chain having a molecular weight less than about 5000; $R_3$ is either an alkyl group, an aryl group, an alkyloxide group or an alkyl sulfide group; $R_6$ is selected from an alkyl group, or an aryl group; and n is a positive integer.

It is preferred that the polymer of the present invention biodegrade following the release of a loaded pharmaceutical compound. More preferably, the polymer of the present invention should biodegrade into substances that are naturally produced or naturally found within the biological systems of animals. For example, the presence of the ester of formula (I) allows the molecule to biodegrade upon hydrolysis, yielding a carboxylic acid and an alcohol.

The compound of the present invention preferably contains polymethylene spacers. When $R_1$, $R_3$, $R_5$ and $R_6$ are polymethylene groups, a preferred compound of the present invention is represented by formula (II)

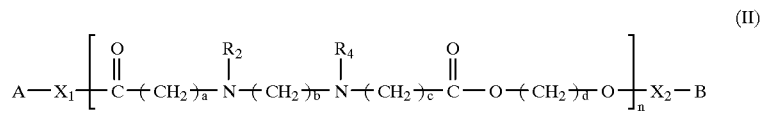

(II)

wherein $X_1$ is —$(CH_2)_b NR_4(CH_2)_c COO(CH_2)_d O$—; $X_2$ is —$OC(CH_2)_a NR_2(CH_2)_b$—; and a, b, c and d each independently range from 1 to about 10.

A polymer of the present invention is biocompatible because it degrades into biologically inert products, preferably naturally occurring or similar products, that are readily removed from the body. One such preferred embodiment of the invention is a polymer consisting of repeating units of spermic acid and biocompatible alcohols, as represented by formula (III)

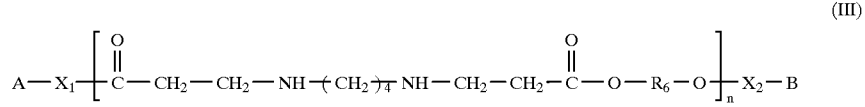

(III)

wherein $X_1$ is —$(CH_2)_4 NH(CH_2)_2 COO(R_6)O$—; and $X_2$ is —$OC(CH_2)_2 NH(CH_2)_4$—.

Typically, O—$R_6$—O will consist of a triol, such as glycerol, or a diol moiety. One skilled in the art will realize that a wide range of diols, triols, or other multiple-alcohols would combine with spermic acid to produce similar polymers with similar degradation byproducts. Other examples of alcohol-containing compounds include hexylene glycol and sugars.

In a highly preferred embodiment, the compound of the present invention is poly(butanediol spermate), as represented by formula (IV)

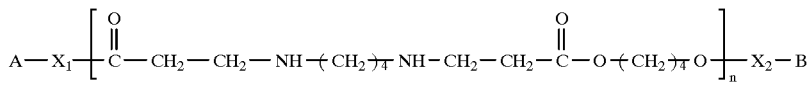

wherein $X_1$ is —$(CH_2)_4NH(CH_2)_2COO(CH_2)_4O$— and $X_2$ is —$OC(CH_2)_2NH(CH_2)_4$—. Hydrolysis of this polymer, represented in FIG. 2, yields the naturally occurring products of spermic acid and 1,4-butanediol.

It is preferable that a carrier of the present invention biodegrade into substances that are naturally produced or naturally found within the biological system of mammals because they are unlikely to be as harmful as foreign substances. Spermic acid, for example, is a natural product which comes from the metabolism of polyamines—such as spermidine and spermine—via oxidative deamination. Spermic acid has also been reported as existing in brain tissue, nervous tissue and urine of various animals. Furthermore, spermic acid can be easily excreted out of the body without accumulation.

Figure 3:
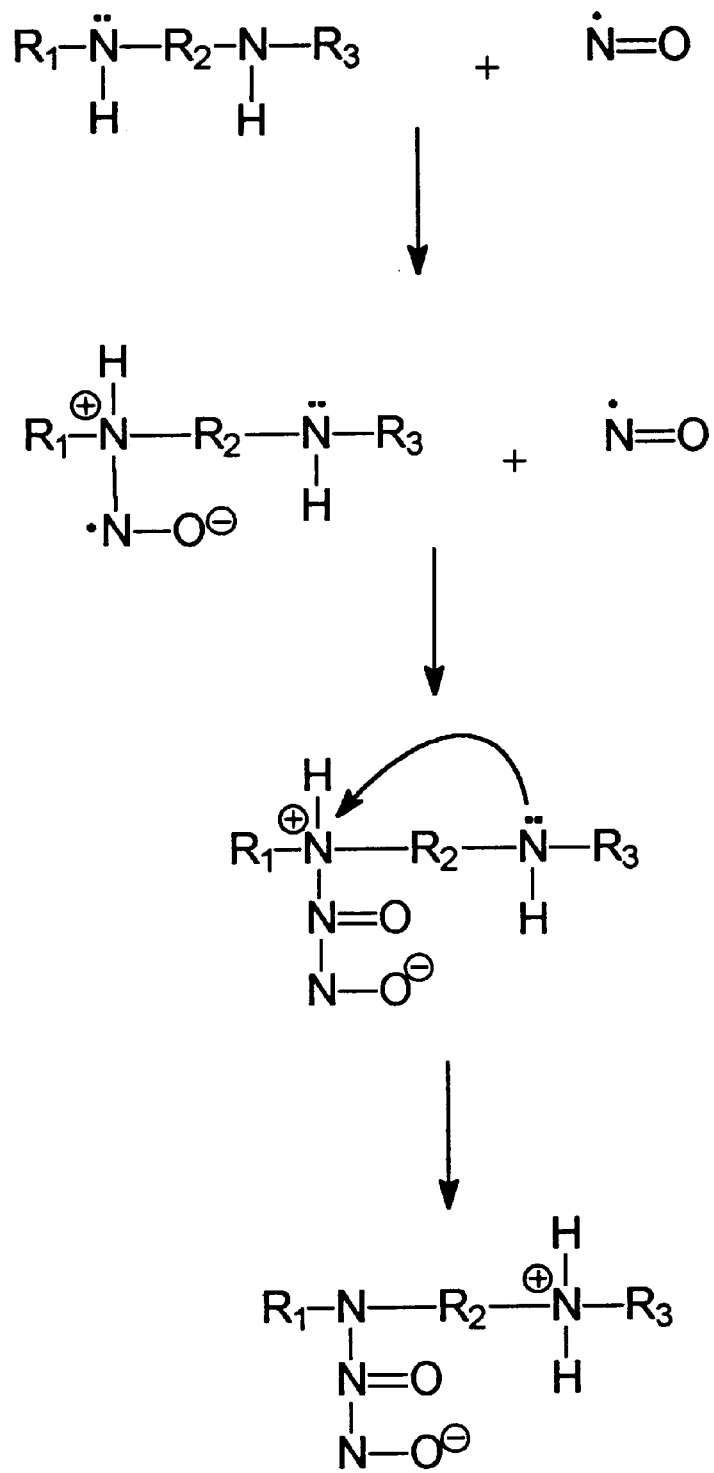
FIG. 3 is the mechanism believed to represent NONOate formation by the stepwise addition of nitric oxide.
Figure 4:
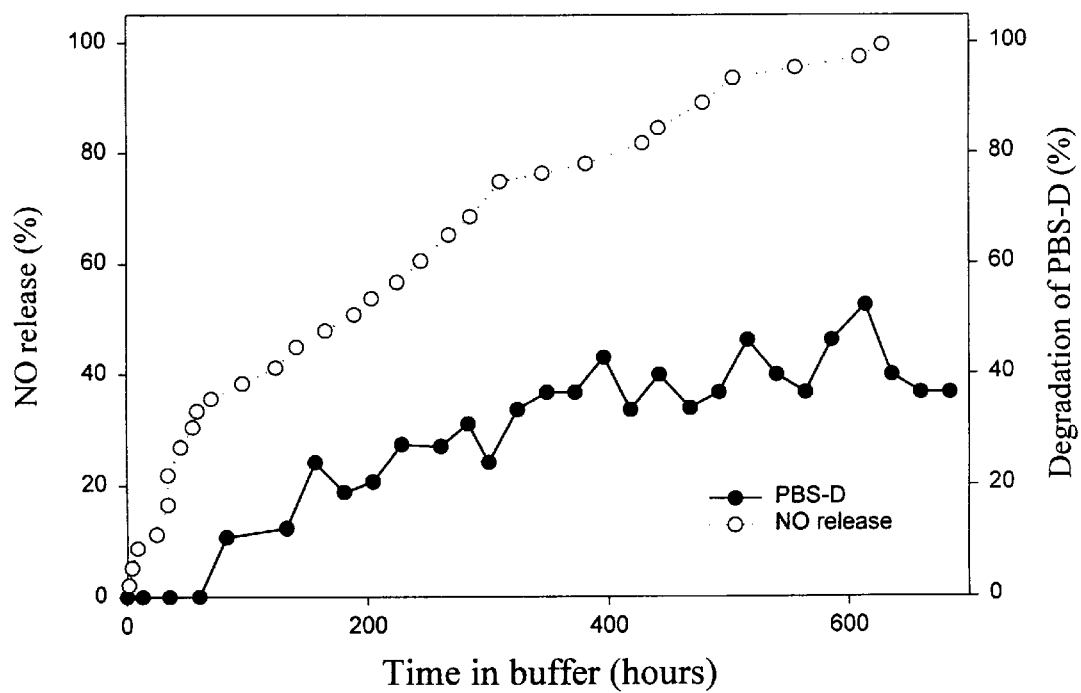
FIG. 4 compares the release profile of nitric oxide from poly(butanediol spermate) diazeniumdiolate (PBS-D) with the degradation of ester bonds in the polymer at 37° C., pH 5.0.

In another embodiment of the present invention, a polymer represented by formulas I, II, III, or IV is bound to a pharmaceutical compound. Any pharmaceutical compound that can react with secondary amine groups and can be loaded onto the carrier of the present invention is envisioned. Examples of suitable pharmaceutical compounds include amino acids, peptides, proteins, enzyme inhibitors, nucleic acids, and other naturally occurring products. A particularly preferred pharmaceutical compound is NO. NO has many biological effects, and its site-specific delivery has many uses including, for example, vasodilation and suppression of an immune response to an implant. As shown in FIG. 3, two NO molecules can bind to a suitable derivatizable group on the carrier of the present invention such as an amine, to form a diazeniumdiolate. Diazeniumdiolates are generally known, such as described in Keefer et al., U.S. Pat. No. 5,039,705. Under appropriate physiological conditions, the NO dissociates from the carrier, and the pharmacological delivery is then complete. An exemplary release profile is shown in FIG. 4 for the release of NO from poly(butanediol spermate) diazeniumdiolate at 37° C., pH 5.0.

Figure 5A:
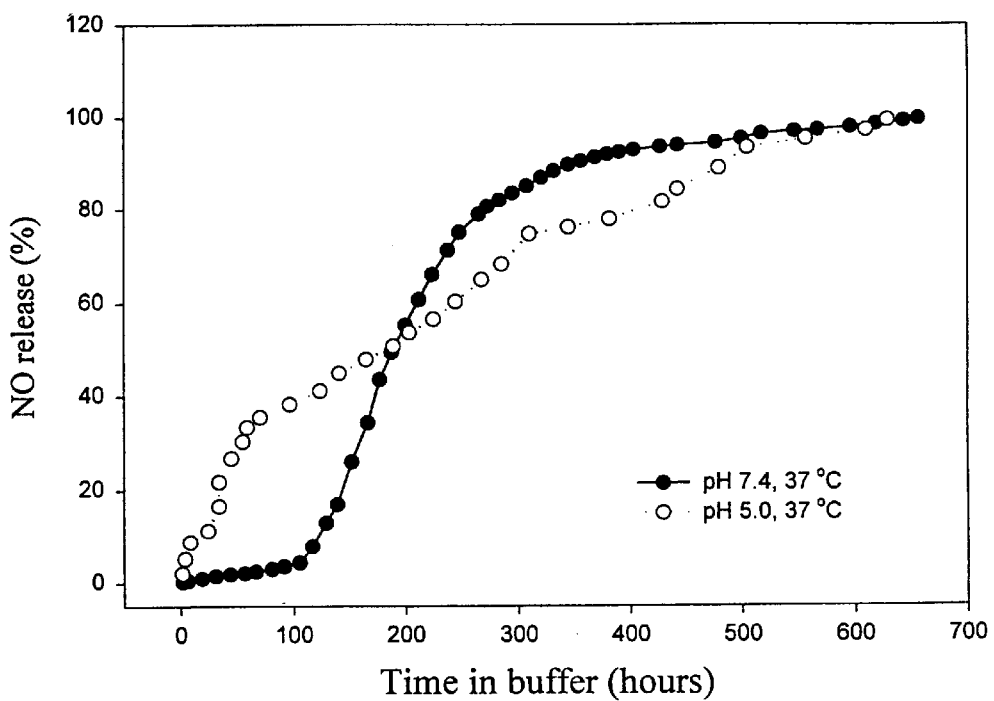
FIGS. 5A and 5B compare NO release from poly (butanediol spermate) diazeniumdiolate at either different pH or different temperatures, respectively.
Figure 5B:
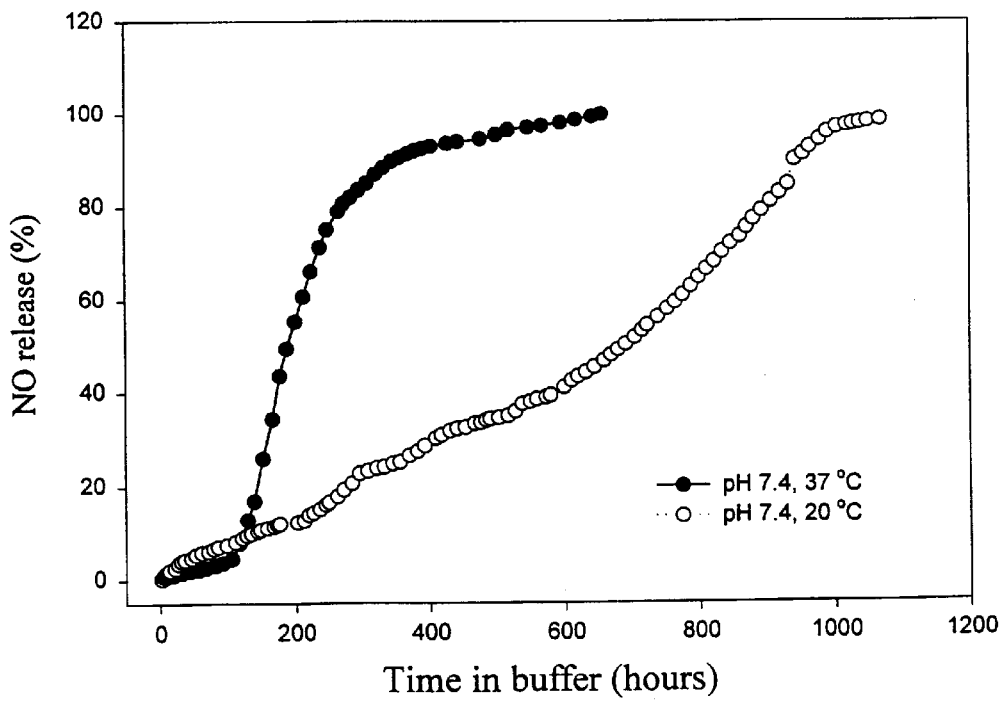
Figure 6:
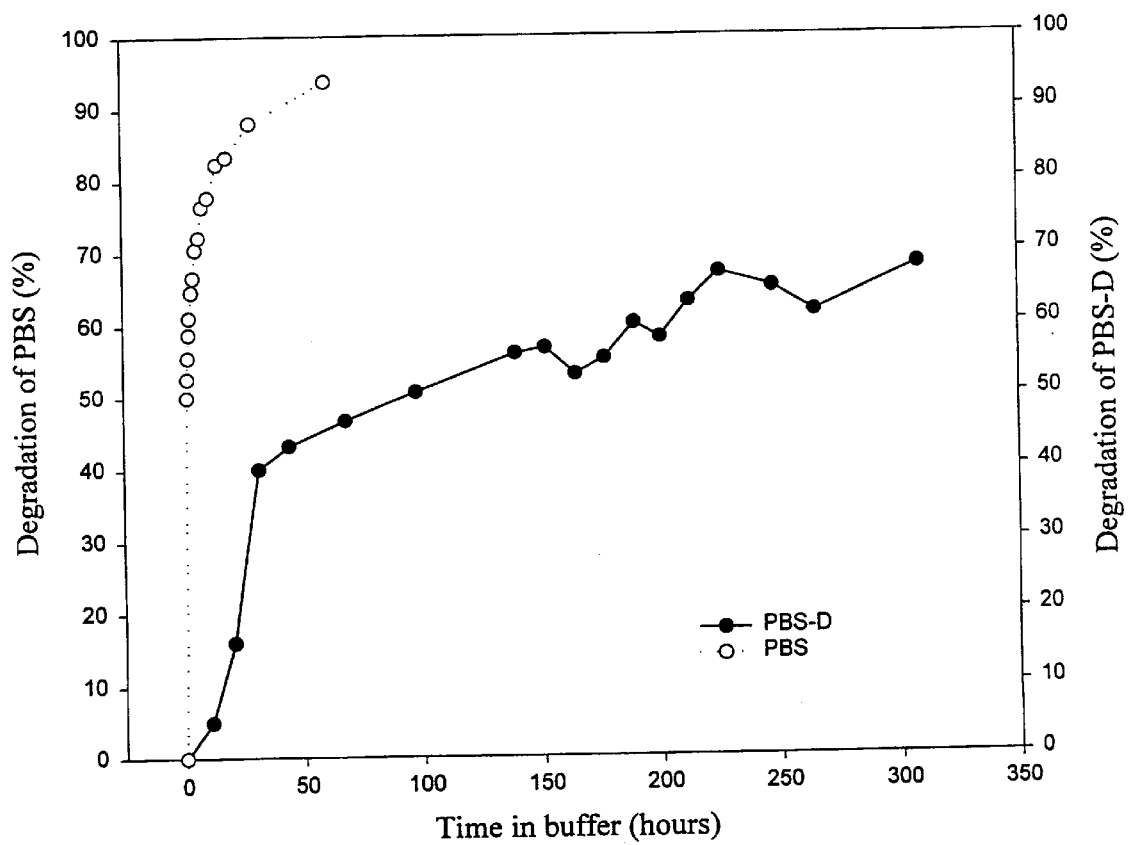
FIG. 6 compares the degradation from the hydrolysis of ester bonds in poly(butanediol spermate) and its diazeniumdiolate at 20° C., pH 7.4.

The rate of NO release is a function of time, temperature, and pH as shown in FIGS. 5A and 5B. NO release is also a function of degradation of its is polymeric carrier—more NO is released with an increase in NO-solvent interaction due to degradation. In turn, degradation of the NO carrier of the present invention is dependent on the extent of NO loading. FIG. 6, for example, shows comparison of rates the degradation of poly(butanediol spermate) and its diazeniumdiolate.

Another embodiment of the present invention is the unpolymerized monomer. As discussed previously, high molecular weight polymers have been used heretofore to deliver NO in vivo. A major drawback to using high molecular weight polymers for NO delivery, or any other use in vivo, is their slow rate of degradation. In addition, rapid and extensive degradation of large polymers is advantageous in many other fields. It would be desirable if diapers, for example, could be made to be biodegradable.

Inserting a monomer or oligomer of the present invention, various embodiments of which are shown in formulas I–IV, into an insoluble polymer allows degradation of the polymer. Although factors other than degradation can cause NO release, FIG. 4 shows a release profile of NO from poly (butanediol spermate) at pH 5.0. Under these conditions, 50% hydrolysis of the polymer occurs in approximately 3.5 hours, as shown in FIG. 1. It is therefore envisioned that this embodiment of the present invention could be incorporated into a cross-linked, urine-absorbing polymer, such as a polysaccharide, thereby rendering soluble an otherwise insoluble polymer, such as found in a diaper.

The compound of formula (I) has the following structure:

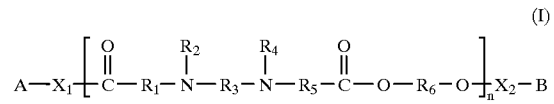

(I)

wherein A is a functional group; $X_1$ is the monomer fragment —$(R_3)NR_4(R_5)COO(R_6)O$—; B is a functional group; $X_2$ is the monomer fragment —$OC(R_1)NR_2(R_3)$—; $R_1$ and $R_5$ are each independently selected from organic groups containing from about 1 to about 10 carbon atoms; $R_2$ and $R_4$ are each independently selected from hydrogen or organic groups containing from 1 to about 20 carbon atoms or a pendant polymer chain having a molecular weight less than about 5000; $R_3$ is independently selected from organic groups containing from 1 to about 10 carbon atoms; $R_6$ is independently selected from organic groups containing from about 1 to about 10 carbon atoms; and n is a positive integer.

To be a suitable cross-linking agent, first, the compound should have relatively high reactivity. Therefore, n is preferably from 0 to about 10. It should be noted that the compound contains one monomeric unit when n is 0. Second, the compound must have at least two polymerizable functional groups, such as a double bond, a peroxy group, or a halide group. Preferably, the polymerizable functional groups are included in A, B, $R_2$, and $R_4$.

EXPERIMENTAL

In order to demonstrate the practice of the present invention, poly(butanediol spermate), was synthesized. The examples set forth hereinbelow, however, are not to be viewed as limiting the disclosure. The claims will serve to define the scope of the invention.

Figure 8:
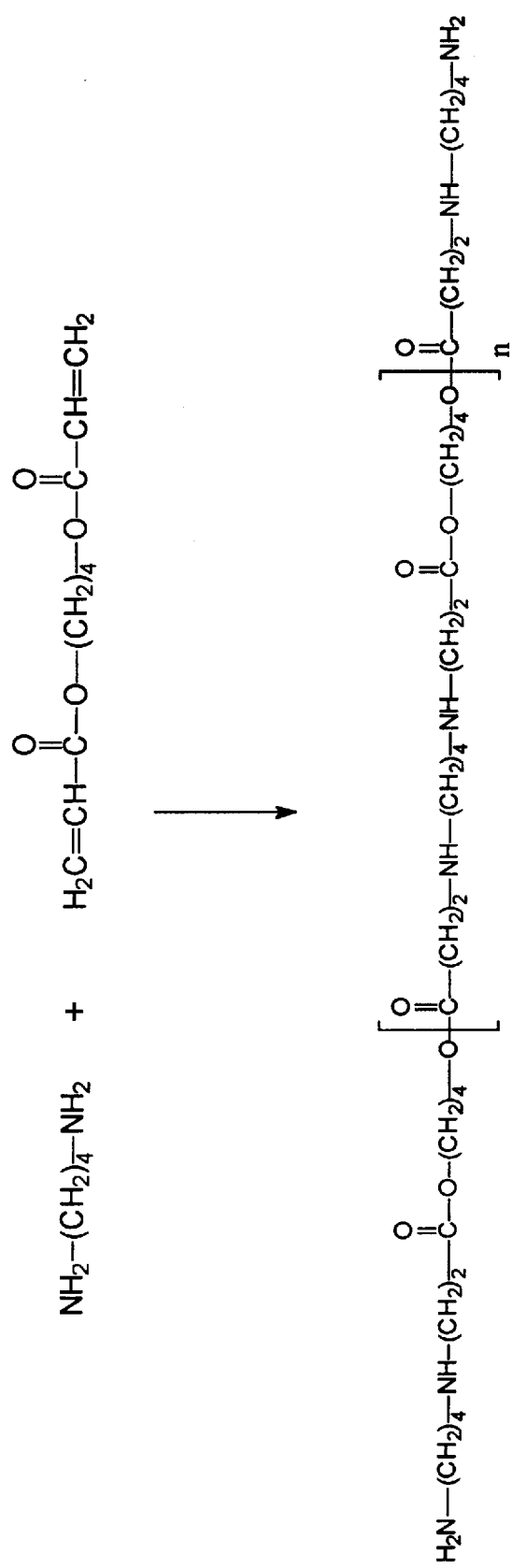
FIG. 8 represents an exemplary polymerization reaction of 1,4-diaminobutane and 1,4-butanedioldiacylate to form poly(butanediol spermate).

The synthesis of poly(butanediol spermate), represented in FIG. 8, was conducted at room temperature by dissolving 2.224 g (0.025 mol) 1,4-diaminobutane (DAB) in 20 ml dried tetrahydrofuran (THF). A solution of 4.950 g (0.025 mol) 1,4-butanediol diacrylate in 15 ml THF was added dropwise into a stirred DAB solution over a period of about 12 hours. The mixed solution was stirred in a round flask for another 24 hours. By rotary evaporation, the THF solvent was completely removed and 6.132 g gel was obtained. The yield was 86%.

The gel obtained was sticky, slightly yellow, and did not redissolve in THF. Neither did it dissolve in dry organic solvents such as acetone, hexane, ether, cyclohexane, dioxane, chloroform, petroleum ether, acetonitrile, or ethanol. It could, however, dissolve in N,N-dimethylformamide (DMF) and in water, with degradation.

By means of gel permeation chromatography (GPC) in DMF, weight-average molecular weight of this polymer was measured to be about 3,000, and the molecular weight distribution was 1.96.

Degradation processes at different pH values (4.83, 7.40, and 9.68) of the polymer is shown in FIG. 1. The percent of retained ester content, compared to original ester content, was determined spectroscopically at room temperature. The percent degradation was then calculated to be 100 minus the percent of retained ester.

To synthesize the diazeniumdiolates of poly(butanediol spermate) the polymer sample was suspended in dried acetonitrile and the solvent discarded. This process was repeated three times in an attempt to eliminate lower molecular weight impurities. Then the swollen polymer was suspended in 80 ml acetonitrile and pressurized under 100 PSI gaseous nitric oxide with stirring in a specially coated storage bottle. The pressure was maintained over three days of reaction time. The yellow product was separated by filtration and dried in vacuo at room temperature. This yellow product, verified by UV spectroscopy to be poly (butanediol spermate) diazeniumdiolate, was insoluble in water and the organic solvents mentioned above.

Using a chemiluminescent method, nitric oxide release profiles in pH 5.0 or 7.4 buffer at 20° C. or 37° C. are shown in FIGS. 5A and 5B. FIG. 5A shows that NO release is much slower at pH 7.4 compared to pH 5.0 over the first 100 hours. FIG. 5B indicates that nitric oxide release is first order and much faster at 37° C. than 20° C. after a delay over approximately the first 100 hours.

The comparison of hydrolysis of ester bonds in poly (butanediol spermate) and its diazeniumdiolate in pH 7.4 buffer is shown in FIG. 6 by measuring the formation of spermic acid, a proxy for degradation, over time. Surprisingly, for the diazeniumdiolate, the degradation rate of the polymer is slowed down substantially. Apparently, the formation of a diazeniumdiolate has a stabilizing effect.

Figure 7:
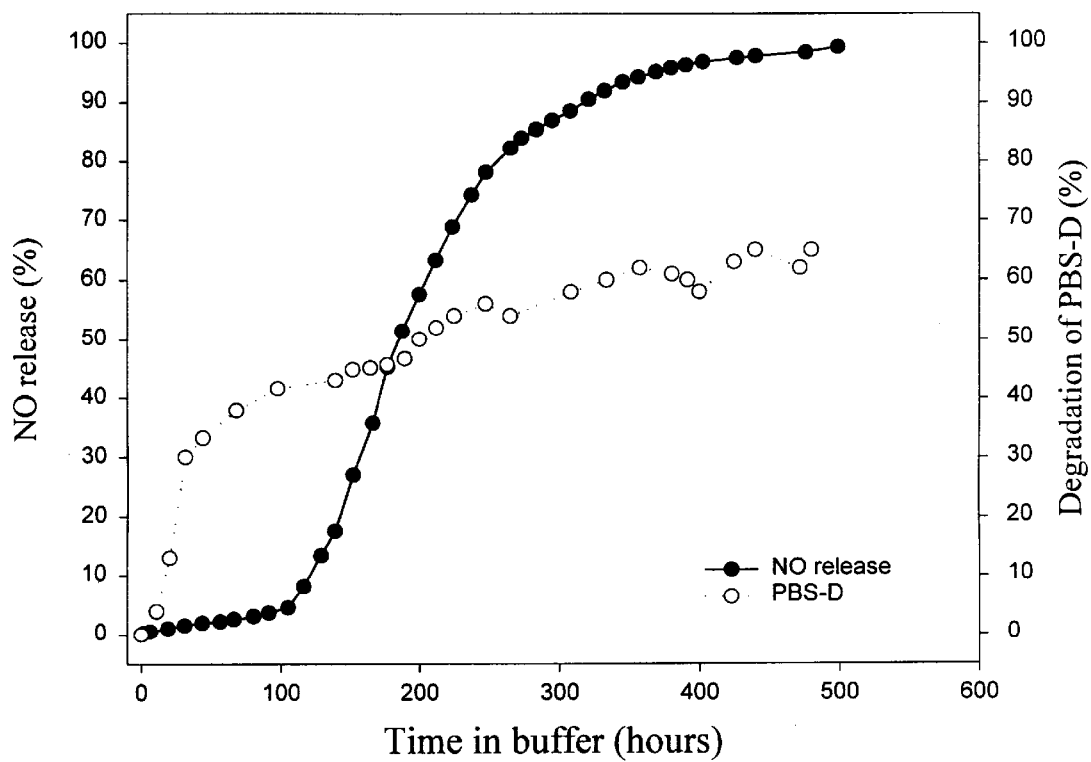
FIG. 7 compares the release of NO to the degradation of poly(butanediol spermate) diazeniumdiolate at 37° C, pH 7.4.

The relationship between nitric oxide release and formation of spermic acid from poly(butanediol spermate) due to hydrolysis in pH 7.4 buffer at 37° C. is shown in FIG. 7. This figure indicates that a substantial amount of ester is hydrolyzed before much nitric oxide is released.

In contrast, nitric oxide release and polymer degradation profile in acidic (pH 5.0) buffer at 37° C. is shown in FIG. 4. This figure shows that a substantial release of nitric oxide precedes the degradation of polymer. Apparently, the low pH stabilizes the polymer. As an aside, it should be noted that it took about 62 hours for the polymer to "dissolve," as shown in the figure, presumably driven by degradation. Thus, the polymer is considered to be insoluble by one of ordinary skill in the art.

Thus, it can be seen that the objects of the invention have been satisfied by the structure and use of the invention as presented above. While only the best mode of the preferred embodiment of the invention has been presented and described in detail, it is to be understood that the invention is not limited thereto or thereby. Accordingly, for an appreciation of the true scope and breadth of the invention, reference should be made to the following claims.

What is claimed is:

1. A hydrolytically unstable polymer having the formula (I):

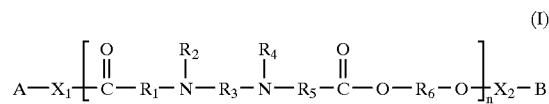

wherein A is a functional group selected from the group consisting of amino and hydroxyl groups; $X_1$ is the monomer fragment —$(R_3)NR_4(R_5)COO(R_6)O$—; B is a functional group selected from the group consisting of amino and hydroxyl groups; $X_2$ is the monomer fragment —$OC(R_1)NR_2(R_3)$—; $R_1$ and $R_5$ are each independently selected from organic groups containing from about 1 to about 10 carbon atoms; $R_2$ and $R_4$ are each independently selected from hydrogen or organic groups containing from 1 to about 20 carbon atoms or a pendant polymer chain having a molecular weight less than about 5000; $R_3$ is independently selected from organic groups containing from 1 to about 10 carbon atoms; $R_6$ is independently selected from organic groups containing from about 1 to about 10 carbon atoms; and n is a positive integer.

2. The polymer according to claim 1, wherein $R_1$ and $R_5$ are each independently selected from the group consisting of an alkyl, an aryl, an alkyl halide, and an aryl halide; $R_2$ and $R_4$ are each independently selected from the group consisting of hydrogen, an alkyl, an aryl, and a pendant polymer chain having a molecular weight less than about 5000; $R_3$ is selected from the group consisting of an alkyl, aryl, alkyloxide and alkyl sulfide; and $R_6$ is selected from an alkyl or an aryl.

3. The polymer according to claim 1, wherein the carrier has the formula (II):

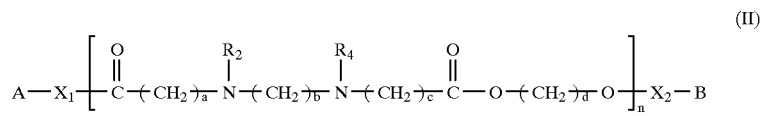

wherein $X_1$ is —$(CH_2)_b NR_4(CH_2)_c COO(CH_2)_d O$—; $X_2$ is —$OC(CH_2)_a NR_2(CH_2)_b$—; and a, b, c and d each independently range from 1 to about 10.

4. The polymer according to claim 1, wherein the carrier has the formula (III):

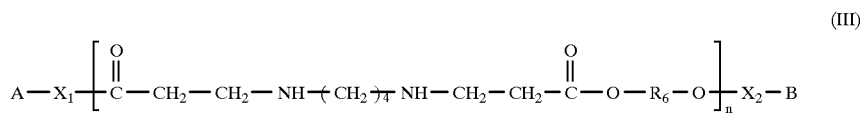

wherein $X_1$ is $-(CH_2)_4NH(CH_2)_2COO(R_6)O-$; and $X_2$ is $-OC(CH_2)_2NH(CH_2)_4-$.

5. The polymer according to claim 1, wherein the carrier has the formula:

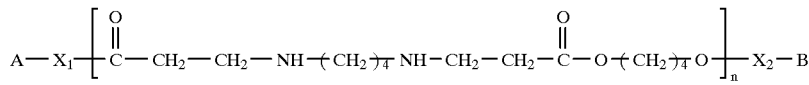

wherein $X_1$ is $-(CH_2)_4NH(CH_2)_2COO(CH_2)_4O-$ and $X_2$ is $-OC(CH_2)_2NH(CH_2)_4-$.

6. A loaded polymer comprising the polymer according to claim 1, wherein a pharmaceutical compound is substituted for at least one of $R_2$ and $R_4$.

7. A loaded polymer comprising the polymer according to claim 2, wherein a pharmaceutical compound is substituted for at least one of $R_2$ and $R_4$.

8. A loaded polymer comprising the polymer according to claim 3, wherein a pharmaceutical compound is substituted for at least one of $R_2$ and $R_4$.

9. The loaded polymer according to claim 6, wherein the pharmaceutical compound is nitric oxide.

10. A method of delivering a pharmaceutical compound in vivo comprising providing a carrier having the formula (I):

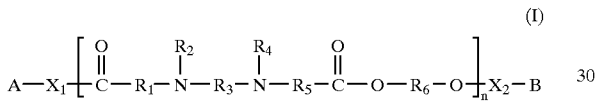

wherein A is a functional group selected from the group consisting of amino and hydroxyl groups; $X_1$ is the monomer fragment $-(R_3)NR_4(R_5)COO(R_6)O-$; B is a functional group selected from the group consisting of amino and hydroxyl groups; $X_2$ is the monomer fragment $-OC(R_1)NR_2(R_3)-$; $R_1$ and $R_5$ are each independently selected from organic groups containing from about 1 to about 10 carbon atoms; $R_2$ and $R_4$ are each independently selected from hydrogen or organic groups containing from 1 to about 20 carbon atoms or a pendant polymer chain having a molecular weight less than about 5000; $R_3$ is independently selected from organic groups containing from 1 to about 10 carbon atoms; $R_6$ is independently selected from organic groups containing from about 1 to about 10 carbon atoms; and n is a positive integer;

loading a pharmaceutical compound onto the carrier; and placing the loaded carrier in vivo, wherein the pharmaceutical compound dissociates from the carrier in vivo.

11. A hydrolytically unstable cross-linking agent comprising a compound having the formula (I):

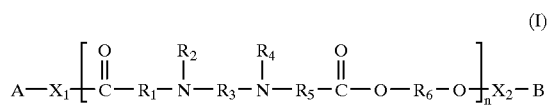

wherein A is a functional group selected from the group consisting of amino and hydoxyl groups; $X_1$ is the monomer fragment $-(R_3)NR_4(R_5)COO(R_6)O-$; B is a functional group selected from the group consisting of amino and hydroxyl groups; $X_2$ is the monomer fragment $-OC(R_1)NR_2(R_3)-$; $R_1$ and $R_5$ are each independently selected from organic groups containing from about 1 to about 10 carbon atoms; $R_2$ and $R_4$ are each independently selected from hydrogen or organic groups containing from 1 to about 20 carbon atoms or a pendant polymer chain having a molecular weight less than about 5000; $R_3$ is independently selected from organic groups containing from 1 to about 10 carbon atoms; $R_6$ is independently selected from organic groups containing from about 1 to about 10 carbon atoms; and n is an integer from 0 to about 10, wherein at least one of A, B, $R_2$, and $R_4$ has one or more polymerizable functional groups such that the compound has at least two polymerizable functional groups.

* * * * *